(12) United States Patent
Learmonth

(10) Patent No.: US 7,241,886 B2
(45) Date of Patent: Jul. 10, 2007

(54) METHOD FOR PREPARATION OF 10,11-DIHYDRO-10-HYDROXY-5H-DIBENZ/B, F/AZEPINE-5-CARBOXAMIDE AND 10,11-DIHYDRO-10-OXO-5H-DIBENZ/B, F/AZEPINE-5-CARBOXAMIDE

(75) Inventor: David Alexander Learmonth, Maia (PT)

(73) Assignee: Portela & C.A., S.A. (PT)

( * ) Notice: Subject to any disclaimer, the term of this patent is extended or adjusted under 35 U.S.C. 154(b) by 497 days.

(21) Appl. No.: 10/478,770

(22) PCT Filed: May 22, 2002

(86) PCT No.: PCT/GB02/02356

§ 371 (c)(1),
(2), (4) Date: Feb. 5, 2004

(87) PCT Pub. No.: WO02/096881

PCT Pub. Date: Dec. 5, 2002

(65) Prior Publication Data

US 2004/0158060 A1    Aug. 12, 2004

(30) Foreign Application Priority Data

May 25, 2001 (GB) ................................. 0112812.3

(51) Int. Cl.
*C07D 223/22* (2006.01)
*A61K 31/55* (2006.01)
*A61P 25/08* (2006.01)

(52) U.S. Cl. ....................... 540/576; 540/589

(58) Field of Classification Search ................ 540/576, 540/589
See application file for complete search history.

(56) References Cited

U.S. PATENT DOCUMENTS 5,753,646 A    5/1998   Benes et al. ................. 514/217

FOREIGN PATENT DOCUMENTS

| CH | 642950  | 5/1984  |
|----|---------|---------|
| DE | 2246842 | 4/1973  |
| NL | 7902811 | 10/1979 |

OTHER PUBLICATIONS

K.M. Baker, J. Csetenyi, A. Frigerio, P.L. Morselli: "10, 11-Dihydro-10, 11-dihydroxy-5H-dibenz(b,f)azepine-5-carboxamide, a metoabolite of carbamazephine isolated from human and rat urine", J. of Med. Chemistry, vol. 16, No. 6, 1973, pp. 703-705, XP002209649.

L. Canali, D.C. Sherrington, H. Deleuze: "Synthesis of resins with pendently-bound chiral manganese-salen complexes and use as heterogeneous asymmetric alkene epoxidation catalysts" Reactive and Functional Polymers, Elsevier Science Publishers, vol. 40, No. 2, May 15, 1999, pp. 155-168, XP004164106, ISSN: 1381-5148.

C.H. Senanayake et al: "The Role of 4-(3-Phenylpropyl)pyridine N-Oxide (P3NO) in the Managanese-Salen-Catalyzed AsymmetRic Epoxidation of Indene" Tetrahedron Letters, Elsevier Science Publishers, vol. 37, No. 19, May 6, 1996, pp. 3271-3274, XP004029376, ISSN: 0040-4039.

G. Bellucci, G. Berti, C. Chiappe, A. Lippi, F. Marioni: "The metaolism of carbamazephine in humans: Steric course of the enzymatic hydrolysis of the 10, 11-epoxide", J. Med. Chem., Am. Chem. Soc., vol. 30, 1987, pp. 768-773, XP002209650.

M. Oshina, H. Yamazaki, I. Shimizu, M. Nisar, J. Tsuji: "Palladium-catalyized selective hydrogenolysis of alkenyloxiranes with formic acid. Stereoselectivity and synthetic utility", J. Am. Chem. Soc., Am. Chem. Soc., vol. 111, 1989, pp. 6280-6287, XP002209651.

E.J. Corey, E.P. Barrette, P.A. Magriotis: "A new Cr(IV) reagent for the catalytic oxidation of secondary alcohols to ketones", Tetrahedron Letters, Pergamon Press Ltd., vol. 26, No. 48, 1985, pp. 5855-5858, XP001095121.

S.M. Grant, D. Faulds.: "Oxcarbazepine. A review of its pharmacology and therapeutic potential in elipepsy, Trigeminal neuralgia and affective disorders", Drugs, Adis International Ltd., vol. 43, No. 6, 1992, pp. 873-888, XP002039768, ISSN: 0012-6667.

J. Benes et al: "Anticonvulsant and sodium channel-blocking properties of Novel 10, 11-Dihydro-5H-dibenz(b,f)azepine-5-carboxamide derivitives" J. of Medicinal Chem., Am. Chem. Soc., vol. 42, 1999, pp. 2582-2587, XP002206156, ISSN; 0022-2623.

S.-I. Murahashi, T. Naota, Y. Oda, N. Hirai: "Ruthenium catalysed oxidation of alcohols with peracids", Synlett, vol. 7, 1995, pp. 733-734XP001093973.

*Primary Examiner*—Brenda Coleman
(74) *Attorney, Agent, or Firm*—Rankin, Hill, Porter & Clark LLP

(57) ABSTRACT

A method for the preparation of 10,11-dihydro-10-hydroxy-5H-dibenz/b,f/azepine-5-carboxamide and 10,11-dihydro-10-oxo-5H-dibenz/b,f/azepine-5-carboxamide from carbamazepine via a three-step process involving (i) epoxidation of carbamazepine; (ii) ring-opening of the resulting epoxide and (iii) oxidation of the resulting alcohol

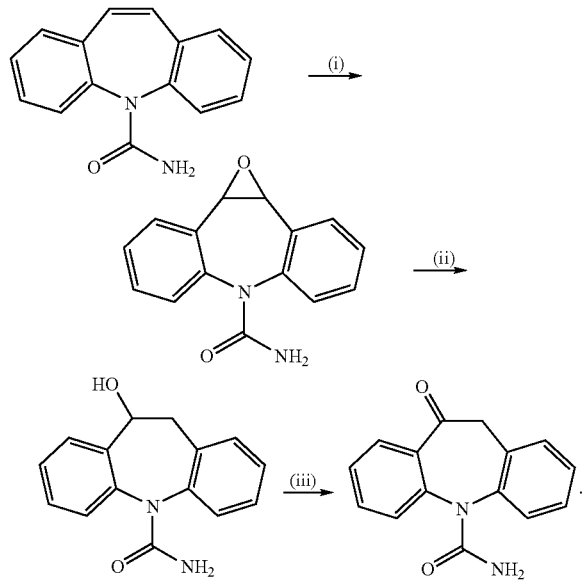

28 Claims, No Drawings

METHOD FOR PREPARATION OF 10,11-DIHYDRO-10-HYDROXY-5H-DIBENZ/B, F/AZEPINE-5-CARBOXAMIDE AND 10,11-DIHYDRO-10-OXO-5H-DIBENZ/B, F/AZEPINE-5-CARBOXAMIDE

This application is a national stage entry under 35 U.S.C. § 371 of PCT/GB02102356, filed May 22, 2002.

The present invention relates to a process for the preparation of 10,11-dihydro-10-hydroxy-5H-dibenz/b,f/azepine-5-carboxamide (1) and 10,11-dihydro-10-oxo-5H-dibenz/b,f/azepine-5-carboxamide (2). Compound (2), known as oxcarbazepine, possesses valuable properties for the treatment of epilepsy and is claimed to be a better-tolerated drug than carbamazepine (compound 3, where R=NH$_2$), a structurally-related anticonvulsant drug (Grant, S. M. et al., Drugs, 43, 873-888 (1992)). Compound (1) is also a known compound with anticonvulsant activity and is in fact the major metabolite of (2) (Schutz, H. et al., Xenobiotica, 16, 769-778 (1986)).

In addition to their anticonvulsant activities, compounds (1) and (2) serve also as useful intermediates for the preparation of (S)-(−)-10-acetoxy-10,11-dihydro-5H-dibenz/b,f/azepine-5-carboxamide (4), a more recently disclosed anticonvulsant (Benes, J. et al., J. Med. Chem., 42, 2582-2587 (1999)). Therefore, a short, economic, high-yielding and environmentally acceptable process for large-scale preparation of both would be desirable, starting preferably from a common, readily available precursor.

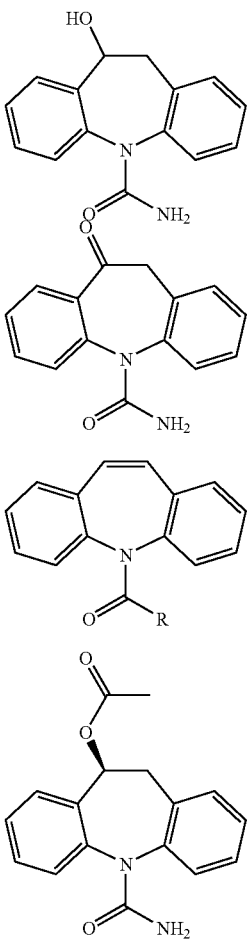

Previously described syntheses of the hydroxy compound (1) have entailed firstly epoxidation of either carbamazepine (i.e. compound 3, where R=NH$_2$) or the chloroanalogue (i.e. compound 3, where R=Cl) using m-chloroperoxybenzoic acid, thus affording the epoxides (i.e. compound 5, where R is NH$_2$ or Cl) in only moderate yield (~60%) (Bellucci, G. et al., J. Med. Chem., 30, 768-773 (1987)). Amination of (6) with ammonia then gives rise to (5).

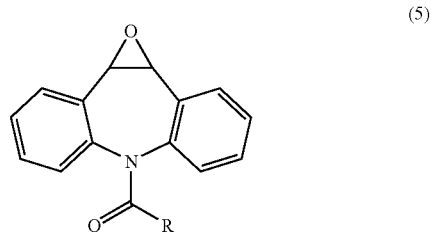

The major drawbacks however are that m-chloroperoxybenzoic acid is potentially explosive and so strict safety measures must accompany its use. Additionally, for this epoxidation a considerable excess of the expensive reagent is necessary. Therefore it is not amenable to large-scale syntheses and indeed many commercial sources have now ceased to produce this hazardous reagent. Other reports of epoxidation of compound (3) include microbial epoxidation (Kittelmann, M. et al., Biosci. Biotechnol. Biochem., 57(9), 1589-1590 (1993); Chem. Abstr. 120:75516), iron porphyrin/peroxide catalysed epoxidation (Yang, S. J. et al., Inorg. Chem., 37(4), 606-607 (1998); (Chem. Abstr. 128:140628), and cobalt-mediated epoxidation with persulfate (Nam, W. et al., Bull. Korean Chem. Soc., 17(5), 414-416 (1996); (Chem. Abstr. 125:86408). These methods are nonetheless unsuitable for large-scale production.

Epoxide (5) is a versatile intermediate. Rearrangement using halides of lithium and magnesium has given direct access to oxcarbazepine (2) (NL 7902811 & HU 63390). These reagents are however moisture-sensitive, are expensive from commercial sources or require preparation in situ, and yields of (2) are often low to moderate. Alternatively, the epoxide (5) has been converted to the alcohol (1) by catalytic hydrogenation using palladium (Baker, K. M. et al., J. Med. Chem., 16(6), 703-705 (1973)). However the catalyst loadings were very high and the overall yield of the alcohol was only moderate.

Oxcarbazepine has been manufactured by a number of processes using different starting materials (WO9621649 & WO0055138). However its preparation by direct oxidation of the alcohol (1) has not been described.

It may be summarised therefore that there is lacking in the prior art an economical, scaleable and high-yielding method useful for the preparation of 10,11-dihydro-10-hydroxy-5H-dibenz/b,f/azepine-5-carboxamide (1) and 10,11-dihydro-10-oxo-5H-dibenz/b,f/azepine-5-carboxamide (2) from the same starting material, carbamazepine (3), which is cheap and readily available in large quantities.

It is an object of the invention to provide an improved method for the preparation of 10,11-dihydro-10-oxo-5H-dibenz/b,f/azepine-5-carboxamide (2) from 10,11-dihydro-10-hydroxy-5H-dibenz/b,f/azepine-5-carboxamide (1). A particular object of the invention is to provide a method which avoids the disadvantages of the prior art.

Thus the present invention provides methods for the preparation of 10,11-dihydro-10-hydroxy-5H-dibenz/b,f/azepine-5-carboxamide (1) and 10,11-dihydro-10-oxo-5H-dibenz/b,f/azepine-5-carboxamide (2) from carbamazepine (3) via a three-step process involving (i) epoxidation of carbamazepine; (ii) ring-opening of the resulting epoxide and (iii) oxidation of the resulting alcohol. In accordance with the present invention, the steps of these process may be performed individually or in combination. Thus, the invention provides a process involving steps (i), (ii) and (iii) individually. The invention further provides a process involving just steps (i) and (ii) or just steps (ii) and (iii). Finally, the invention provides a process involving all three steps (i), (ii) and (iii).

The steps (i), (ii) and (iii) will now be described in more detail.

Step (i)

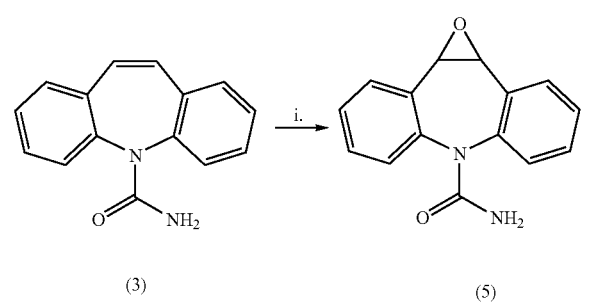

(3)    (5)

The epoxidation of carbamazepine is desirably carried out by addition of excess peroxyacetic acid to a stirred suspension of carbamazepine (3) and a metal catalyst in an inert solvent. The reaction may be carried out in the presence of an inorganic base. Peroxyacetic acid is cheap and readily available commercially as a solution in acetic acid or can be prepared in situ from mixtures of acetic acid and hydrogen peroxide (Hudlicky, M. Oxidations in Organic Chemistry, ACS Monograph, Washington DC, 1990). Preferably 1.5-3 molar equivalents of peroxyacetic acid are used.

Suitable inert solvents include chlorinated hydrocarbons. The inorganic base may be, for example, sodium acetate, sodium carbonate and potassium carbonate, all of which are readily available and inexpensive; it is preferred that 2.5-3.2 molar equivalents of the inorganic base are used. Several metal catalysts are suitable for the epoxidation reaction including complexes of manganese, cobalt, nickel, copper, rhodium and iron.

Preferred catalysts include manganese (III) salen, manganese (III) acetylacetonate, manganese(IV) oxide and potassium permanganate. Normally, 0.025-3 mol % of catalyst is desirable for good conversion. If preferred, a phase-transfer catalyst such as, for example Adogen 464 or Aliquat 336 may be used. If desired, the metal catalyst may be supported on an inert support such as alumina, silica or inert clay, in the form of powders, pellets or beads allowing for better recovery after reaction by simple filtration, an important factor due to environmental issues. Normally a 2-4% w/w supported catalyst is preferable.

Alternatively and if desired, the order of addition of the reagents may be reversed and carbamazepine (3) may be added to a solution of peroxyacetic acid and catalyst in the preferred solvent system. In either case, after the mildly exothermic reaction is complete, the inorganic base and supported metal catalyst may be removed by filtration and the filtrate may be stirred with aqueous sodium sulphite solution to destroy excess peroxide. The organic phase may then be separated, washed with water and sodium bicarbonate. The crude epoxide (5) may be obtained by evaporation of the organic solvent and can be purified, if desired, from a suitable solvent such as ethyl acetate or alcohols having from 1 to 6 carbon atoms, such as ethanol or isopropanol. The yield is usually above 85% and the product is usually >97% pure by HPLC analysis.

Step (ii)

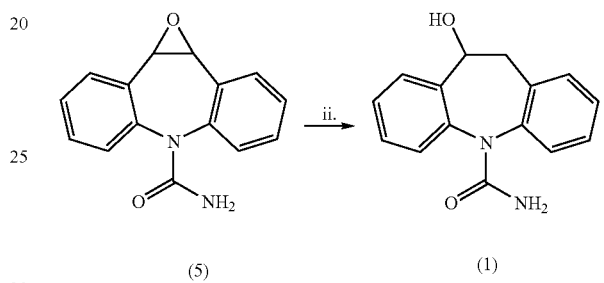

(5)    (1)

The ring-opening of the epoxide (5) may be simply carried out by either catalytic hydrogen transfer or catalytic hydrogenation. We have found that by careful selection of the conditions of the reaction it is possible to obtain unexpectedly high yields. For catalytic hydrogen transfer, a suitable catalyst is added to a solution of the epoxide and a hydrogen donor in a suitable solvent mixture and the mixture is stirred at room temperature until reaction is complete.

The preferred catalyst is palladium, preferably adsorbed on an inert support such as charcoal and normally 0.1-1 mol % of 5-10 w % palladium on the support is used. Preferably there is 0.2-1 mol %, most preferably 0.25-0.4 mol %, of 5-10 w % palladium on the support. More preferably there is 5-7 w % palladium on the support. We have found that the optimum selection of the catalyst improves the yield of the reaction.

Preferred hydrogen donors include cyclohexene, formic acid, sodium formate and ammonium formate, and 1.5-3 molar equivalents are usually used.

Preferred solvents for the reaction include chlorinated alkanes, such as dichloromethane, alcohols having from 1 to 6 carbon atoms, such as methanol, ethanol or isopropanol, and water, or the reaction can be run in mixtures of the above mentioned solvents. We have obtained the best results with dichloromethane, methanol and water. The addition of water (preferably in an amount of 1 volume to the epoxide) has been found to improve the reaction by reducing side products.

It is preferred that the reaction is carried out at ambient temperature, i.e., 15-25° C.

After the reaction is complete, the catalyst may be recovered by filtrabon through celite or silica, and the filtrate may be evaporated under vacuum. If desired, the crude product may be recrystallised from a suitable solvent such as ethyl acetate or lower alcohols such as ethanol.

For catalytic hydrogenation, a suitable catalyst is added to a stirred solution of the epoxide (5) in a suitable solvent mixture, containing an optional organic base. Suitable catalysts and solvent mixtures are the same as described above in relation to the catalytic hydrogen transfer reaction. We have obtained the best results with methanol (in about 20 volumes to the epoxide) and water (in about 1 volume to the epoxide), the best results being obtained when both methanol and water are used. The addition of water (preferably in an amount of 1 volume to the epoxide) has been found to improve the reaction by reducing side products. We have also found that the reaction can be improved by the use of an organic base, especially trialkylamines, such as triethylamine. This speeds the reaction up, thus resulting in the formation of fewer side products and greater yield. The best concentration of the organic base is 3-4 molar equivalents to the epoxide. The reaction can be carried out at different temperatures and pressures, though atmospheric pressure and ambient temperature (15-25° C.) are preferred. Hydrogen gas may be bubbled through the reaction mixture, and, on completion of the reaction (1-3 hours), the catalyst may be recovered by filtration and the product may be isolated as described above in relation to the catalytic hydrogen transfer.

Yields in both the catalytic hydrogen transfer and the catalytic hydrogenation reactions are usually in the range 85-95% and product purity usually >97%.

Step (iii)

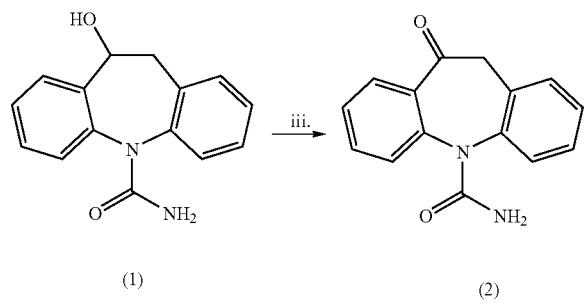

Oxidations of simple alcohols with peracids in conjunction with metal catalysts have been reported in the chemical literature (ruthenium catalysed: Murahashi, S. I. et al., Synlett, 7, 733-734 (1995)), (chromate catalysed: Corey, E. J. et al., Tetrahedron Letters, 26(48), 5855-5858 (1985)). Similarly oxidation of simple alcohols with peroxyacetic acid in the presence of sodium bromide has been reported (Morimoto, T. et al., Bull. Chem. Soc. Jpn., 65, 703-706 (1992)). It is more common however, for hydrogen peroxide or t-butyl hydroperoxide to be used as oxidants (e.g. Muzart, J. et al., Synthesis, 785-787, (1993)).

However, in accordance with a particularly advantageous feature of the invention, the oxidation of the alcohol (1) is be carried out by addition of an excess of peroxyacetic acid to a stirred suspension of the alcohol (1) and a metal catalyst in a suitable solvent. If desired, a phase-transfer catalyst such as for example Adogen 464 or Aliquat 336 may be used. Usually 3-5 molar equivalents of peroxyacetic acid are required. Suitable solvents include chlorinated alkanes such as for example, dichloromethane or 1,2-dichloroethane. Preferred metal catalysts are chromium trioxide, manganese dioxide, manganese (III) acetate, potassium permanganate, cobalt (II) chloride and potassium and sodium dichromate.

If desired, the metal catalyst may be supported on an inert support such as alumina, silica or inert clay, in the form of powders, pellets or beads allowing for better recovery after reaction by simple filtration. Normally a 2-4% w/w supported catalyst is preferable and typically 0.5-5 mol % of the metal catalyst is used for the oxidation reaction.

Alternatively and if desired, the order of addition of the reagents may be reversed and the solid alcohol (1) may be added to a solution of peroxyacetic acid and catalyst in the preferred solvent system. After the mildly exothermic reaction is complete, the supported metal catalyst may be removed by filtration and the filtrate may be stirred with aqueous sodium sulphite solution to destroy excess peroxide. The organic phase may then be separated, washed with water and sodium bicarbonate. The crude oxcarbazepine (2) may be obtained by evaporation of the organic solvent and can be purified if preferred from a suitable solvent such as ethyl acetate or alcohols having 1 to 6 carbon atoms such as for example, ethanol or isopropanol. The yield is usually above 85% and the product is usually >97% pure.

According to another aspect of the invention there is provided a process for the production of 10,11-dihydro-10-hydroxy-5H-dibenz/b,f/azepine-5-carboxamide (1) by the reaction of carbamazepine (3) with peroxyacetic acid and a metal catalyst in a substantially inert solvent to produce 1a,10b-dihydro-6H-dibenz/b,f/oxireno[d]azepine-6-carboxamide (5), followed by ring-opening of 1a,10b-dihydro-6H-dibenz/b,f/oxireno[d]azepine-6-carboxamide (5) either by catalytic transfer hydrogenation in the presence of a hydrogen donor and metal catalyst, or alternatively by catalytic hydrogenation with gaseous hydrogen in the presence of a metal catalyst. This process is preferably carried out in accordance with the features described in relation to steps (i) and (ii) above.

According to one aspect of the present invention there is provided a process for the preparation of 10,11-dihydro-10-oxo-5H-dibenz/b,f/azepine-5-carboxamide (2) from 10,11-dihydro-10-hydroxy-5H-dibenz/b,f/azepine-5-carboxamide (1) the process comprising oxidising 10,11-dihydro-10-hydroxy-5H-dibez/b,f/azepine-5-carboxamide (1) by reaction with peroxyacetic acid in the presence of a metal catalyst in a substantially inert solvent.

According to another aspect of the invention there is provided a process for the production of 10,11-dihydro-10-hydroxy-5H-dibenz/b,f/azepine-5-carboxamide (1) by ring-opening of 1a,10b-dihydro-6H-dibenz/b,f/oxireno[d]azepine-6-carboxamide (5), either by catalytic transfer hydrogenation in the presence of a hydrogen donor and metal catalyst, or alternatively by catalytic hydrogenation with gaseous hydrogen in the presence of a metal catalyst. This process is preferably carried out in accordance with the features described in relation to step (ii) above.

According to another aspect of the invention there is provided a process for the production of 1a,10b-dihydro-6H-dibenz/b,f/oxireno[d]azepine-6-carboxamide (5) by the reaction of carbamazepine (3) with peroxyacetic acid and a metal catalyst in a substantially inert solvent. This process is preferably carried out in accordance with the features described in relation to step (i) above.

According to another aspect of the invention there is provided a method for the preparation of a compound of the formula (6):

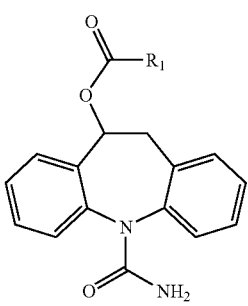

(6)

where R₁ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming 10,11-dihydro-10-hydroxy-5H-dibenz/b,f/azepine-5-carboxamide by a method as described above, then treating the 10,11-dihydro-10-hydroxy-5H-dibenz/b,f/azepine-5-carboxamide to produce the compound of formula (6). The compound of formula (6) is preferably prepared by acylating the 10,11-dihydro-10-hydroxy-5H-dibenz/b,f/azepine-5-carboxamide.

The compound of formula (6) is described in more detail in our U.S. Pat. No. 5,753,646, the contents of which are incorporated herein by reference. The method can be used to produce any of the compounds disclosed in U.S. Pat. No. 5,753,646. For example, to produce 10-acetoxy-10,11-dihydro-5H-dibenz/b,f/azepine-5-carboxamide it is possible to add acetylchloride in dichloromethane to a suspension of 10,11-dihydro-10-hydroxy-5H-dibenz/b,f/azepine-5-carboxamide and pyridine in dichloromethane, as described in example 4, of U.S. Pat. No. 5,753,646.

The compounds described in examples 4 to 17 of U.S. Pat. No. 5,753,646 can be produced by acylation using the appropriate acyl halide. The compounds described in examples 18 to 23 can be produced using the appropriate carboxylic acid.

Using the present invention it is therefore possible to produce the following compounds:

(1) 10-acetoxy-10,11-dihydro-5H-dibenz/b,f/azepine-5-carboxamide
(2) 10-benzoyloxy-10,11-dihydro-5H-dibenz/b,f/azepine-5-carboxamide
(3) 10-(4-methoxybenzoyloxy)-10,11-dihydro-5H-dibenz/b,f/azepine-5-carboxamide
(4) 10-(3-methoxybenzoyloxy)-10,11-dihydro-5H-dibenz/b,f/azepine-5-carboxamide
(5) 10-(2-methoxybenzoloxy)-10,11-dihydro-5H-dibenz/b,f/azepine-5-carboxamide
(6) 10-(4-nitrobenzoyloxy)-10,11-dihydro-5H-dibenz/b,f/azepine-5-carboxamide
(7) 10-(3-nitrobenzoyloxy)-10,11-dihydro-5H-dibenz/b,f/azepine-5-carboxamide
(8) 10-(2-nitrobenzoyloxy)-10,11-dihydro-5H-dibenz/b,f/azepine-5-carboxamide
(9) 10-(4-chlorobenzoyloxy)-10,11-dihydro-5H-dibenz/b,f/azepine-5-carboxamide
(10) 10-(3-chlorobenzoyloxy)-10,11-dihydro-5H-dibenz/b,f/azepine-5-carboxamide
(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyryloxy-10,1-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl)pentanoyloxy]-10,11-dihydro-5H-dibenz/b,f/azepine-5-carboxamide
(16) 10-[(2-ethyl)hexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide
(20) 10-phenylacetoxy-10,11-dihydro-5H-bibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide
(25) 10-nicotinoyloxy-10,11-dihydro-5H-dibenz/b,f/azepine-5-carboxamide
(26) 10-isonicotinoyloxy-10,11-dihydro-5H-dibenz/b,f/azepine-5-carboxamide
(27) 10-chloroacetoxy-10,11-dihydro-5H-dibenz/b,f/azepine-5-carboxamide
(28) 10-bromoacetoxy-10,11-dihydro-5H-dibenz/b,f/azepine-5-carboxamide
(29) 10-formyloxy-10,11-dihydro-5H-dibenz/b,f/azepine-5carboxamide
(30) 10-ethoxycarbonyloxy-10,11-dihydro-5H-dibenz/b,f/azepine-5-carboxamide
(31) 10-(2 chloropropionyloxy-10,11-dihydro-5H-dibenz/b,f/azepine-f-carboxamide The 10,11-dihydro-10-hydroxy-5H-dibenz/b,f/azepine-5-carboxamide may be resolved into its (R)-(+)- and (S)-(−)-stereoisomers, whereby the desired (R)-(+)- or (S)-(−)-stereoisomer of the above compounds may be produced.

These compounds, or pharmaceutically acceptably derivatives thereof (such as salts), can be used in the preparation of pharmaceutical compositions comprising the compound itself, or the derivative, in combination with a pharmaceutically acceptable carrier. Such compositions have anticonvulsant properties and can be used in the treatment of some central and peripheric nervous system disorders, such as epilepsy.

The invention disclosed herein will be exemplified by the following examples of preparation, which should not be construed to limit the scope of the disclosure. It is to be understood that the invention is not to be limited to the exact details of operation as obvious modifications and equivalents will be apparent to those skilled in the art.

EXAMPLE 1

1a,10b-Dihydro-6H-dibenz/b,f/oxireno[d]azepine-6-carboxamide (5)

To a stirred suspension of carbamazepine (3) (200 g, 847.5 mmol) and sodium carbonate (287.4 g, 2711 mmol) in dichloromethane (1000 ml) were added tablets of potassium permanganate supported on alumina (3.5% w/w, 3.46 g, 0.77 mmol). Thereafter, peroxyacetic acid (39% solution in acetic acid, 432 ml, 2538 mmol) was added dropwise over one hour, causing a gradual rise in temperature until gentle reflux of the solvent. The mixture was stirred for twenty minutes and then allowed to stand for twenty minutes. The sodium carbonate and supported catalyst were then removed by filtration and washed by dichloromethane (200 ml); the alumina beads were separated from sodium carbonate by screening through a sieve. The combined filtrate was then stirred with an aqueous solution of sodium sulphite (20 g) and sodium bicarbonate (20 g) in water (250 ml) for one hour. The phases were then separated and the aqueous phase extracted by dichloromethane (50 ml). The combined organic layers were washed by water (100 ml), saturated aqueous sodium bicarbonate (100 ml), water again (100 ml) and brine, then dried over anhydrous sodium sulphate and filtered. Evaporation of the solvent (rotary evaporator, water aspirator pressure, 40° C.) gave the crude epoxide (5) as a beige solid which was crystallised from ethyl acetate (100 ml) to give the product as an off-white solid, 194.2 g, (91% yield).

EXAMPLE 2

10,11-Dihydro-10-hydroxy-5H-dibenz/b,f/azepine-5-carboxamide (1)

(a) Catalytic Hydrogen Transfer

To a solution of the 1a,10b-dihydro-6H-dibenz/b,f/oxireno[d]azepine-6carboxamide (5) (5.03 g, 20 mmol) in methanol (100 ml), dichloromethane (50 ml) and water (5 ml) at room temperature under nitrogen was added ammonium formate (3.78 g, 60 mmol) followed by 10% palladium on charcoal (540 mg, 0.51 mmol Pd). The resulting mixture was stirred at room temperature for one hour and then the catalyst was recovered by filtration through celite. The filter pad was washed with dichloromethane (20 ml), and the organic phase of the combined filtrate was separated and dried over anhydrous sodium sulphate. Filtration and evaporation of the solvent (rotary evaporator, water aspirator pressure, 40° C.) gave the crude alcohol (1) which was crystallised from ethyl acetate (20 ml) to afford white crystals, 4.7 g, (93% yield).

(b) Catalytic Hydrogenation

To a stirred solution of the 1a,10b-dihydro-6H-dibenz/b,f/oxireno[d]azepine-6-carboxamide (5) (50.0 g, 198 mmol) in a mixture of methanol (950 ml) and water (50 ml) and triethylamine (64.8 g, 89 ml, 641 mmol) at room temperature was added 5% palladium on charcoal (1.29 g, 0.61 mmol). Gaseous hydrogen was bubbled through the reaction mixture for two hours at room temperature and atmospheric pressure and then the catalyst was recovered by filtration through celite. The filter pad was washed with dichloromethane (20 ml), and the organic phase of the combined filtrate was separated and dried over anhydrous sodium sulphate. Filtration and evaporation of the solvent (rotary evaporator, water aspirator pressure, 40° C.) gave the crude alcohol (1) which was crystallised from ethyl acetate (100 ml) to afford white crystals, 46.7 g, (93% yield).

EXAMPLE 3

10,11-Dihydro-10-oxo-5H-dibenz/b,f/azepine-5-carboxamide (2)

To a stirred suspension of 10,11-dihydro-10-hydroxy-5H-dibenz/b,f/azepine-5-carboxamide (1) (100 g, 394 mmol) in 1,2-dichloroethane (1000 ml) at room temperature was added potassium dichromate adsorbed on silica gel (46.0 g, (0.34 mmol/g, 15.6 mmol). Thereafter, peroxyacetic acid (300 ml, 39% solution in acetic acid, 1425 mmol) was added dropwise; the reaction became purple in appearance and a gently exothermic reaction set in. After stirring for a further one hour, the silica-supported catalyst was removed by filtration and washed by dichloromethane (100 ml). The combined filtrate was then stirred with an aqueous solution (5%) of sodium sulphite (500 ml) for one hour. The phases were then separated and the aqueous phase was extracted by dichloromethane (50 ml). The combined organic layers were washed by water (100 ml), saturated aqueous sodium bicarbonate (100 ml), water again (100 ml) and brine, then dried over anhydrous sodium sulphate and filtered. Evaporation of the solvent (rotary evaporator, water aspirator pressure, 40° C.) afforded the crude product (2) as an off-white solid which was crystallised from ethanol to afford white crystals, 89.5 g (90% yield).

It will be appreciated that the invention described above may be modified.

The invention claimed is:

1. A process for the preparation of 10,11-dihydro-10-hydroxy-5H-dibenz[b,f]azepine-5-carboxamide comprising the steps of: reacting carbamazepine with peroxyacetic acid and a metal catalyst in a substantially inert solvent to produce 11a,10b-dihydro-6H-dibenz[b,f]oxireno[d]azepine-6-carboxamide followed by ring-opening of the 11a,10b-dihydro-6H-dibenz[b,f]oxireno[d]azepine-6-carboxamide, either by catalytic transfer hydrogenation in the presence of a hydrogen donor and metal catalyst, or alternatively by catalytic hydrogenation with gaseous hydrogen in the presence of a metal catalyst to produce the 10,11-dihydro-10-hydroxy-5H-dibenz[b,f]azepine-5-carboxamide.

2. A process according to claim 1, wherein the ring-opening reaction is carried out by catalytic hydrogen transfer using a metal catalyst and hydrogen donor.

3. A process according to claim 2, wherein the hydrogen donor used in the ring-opening reaction is selected from formic acid, cyclohexene, sodium formate and ammonium formate.

4. A process according to claim 1, wherein the ring-opening reaction is carried out by catalytic hydrogenation using gaseous hydrogen the presence of a metal catalyst.

5. A process according to claim 1, wherein the ring-opening reaction is carried out in the presence of an organic base which is a trialkylamine.

6. A process according to claim 1, wherein the metal catalyst used in the ring-opening reaction is 0.1-1 mol% of 5-10w % palladium adsorbed on activated charcoal.

7. A process according to claim 1, wherein the ring-opening reaction is carried out in a solvent selected from chlorinated hydrocarbons, alcohols having from 1 to 6 carbon atoms and water or mixtures thereof.

8. A process according to claim 1, wherein the metal catalyst used in the reaction of carbamazepine is chosen from manganese (III) salen, manganese (III) acetylacetonate, manganese (IV) oxide or potassium permanganate.

9. A process according to claim 1, wherein the metal catalyst used in the reaction of carbamazepine is supported on an inert support, selected from silica gel, alumina, clay or molecular sieves.

10. A process according to claim 1, wherein the reaction of carbamazepine is carried out in the presence of an inorganic base, and the inorganic base is chosen from sodium acetate, sodium carbonate or potassium carbonate.

11. A process according to claim 1, wherein the substantially inert solvent used in the reaction of carbamazepine is a chlorinated hydrocarbon solvent.

12. A process for the production of 10,11-dihydro-10-hydroxy-5H-dibenz[b,f]azepine-5-carboxamide by ring-opening of 11a,10b-dihydro-6H-dibenz[b,f]oxireno[d]azepine-6-carboxamide, either by catalytic transfer hydrogenation in the presence of a hydrogen donor and metal catalyst, or alternatively by catalytic hydrogenation with gaseous hydrogen in the presence of a metal catalyst and in the presence of an organic base.

13. A process according to claim 12, wherein the ring-opening reaction is carried out by catalytic transfer hydrogenation in the presence of an organic base.

14. A process according to claim 13, wherein the organic base used in the catalytic transfer hydrogenation or in the catalytic hydrogenation is a trialkylamine.

15. A process according to claim 12, wherein the metal catalyst used in the ring-opening reaction is 0.1-1 mol % of 5-10 w % palladium adsorbed on activated charcoal.

16. A process for the preparation of a compound of the formula (6):

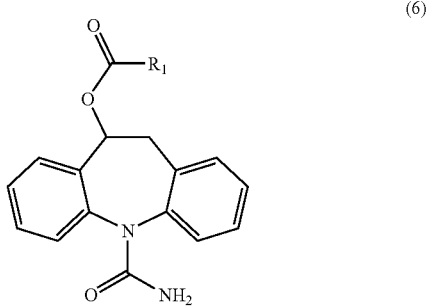

(6)

where R1 is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromine or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming 10,11-dihydro-10-hydroxy-5H-dibenz[b,f]azepine-5-carboxamide by a process according to any preceding claim, then treating the 10,11-dihydro-10-hydroxy-5H-dibenz[b,f]azepine-5-carboxamide to produce the compound of formula (6).

17. A process according to claim 16, wherein the compound of formula (6) is prepared by acylating the 10,11-dihydro-10-hydroxy-5H-dibenz[b,f]azepine-5-carboxamide.

18. A process for the preparation of 10-acetoxy-10,11-dihydro-5H-dibenz[b,f]azepine-5-carboxamide comprising forming 10,11-dihydro-10-hydroxy-5H-dibenz[b,f]azepine-5-carboxamide by a process according to claim 1, then acylating the 10,11-dihydro-10-hydroxy-5H-dibenz[b,f]azepine-5-carboxamide with acetylchloride.

19. A process for the preparation of 10,11-dihydro-10-oxo-5H-dibenz[b,f]azepine-5-carboxamide comprising preparing 10,11-dihydro-10-hydroxy-5H-dibenz[b,f]azepine-5-carboxamide by a process according to claim 1, then oxidising 10,11-dihydro-10-hydroxy-5H-dibenz[b,f]azepine-5-carboxamide by reaction with peroxyacetic acid in the presence of a metal catalyst in a substantially inert solvent.

20. A process for the preparation of 10,11-dihydro-10-oxo-5H-dibenz[b,f]azepine-5-carboxamide from 10,11-dihydro-1 0-hydroxy-5H-dibenz[b,f]azepine-5-carboxamide, the process comprising oxidising 10,11-dihydro-10-hydroxy-5H-dibenz[b,f]azepine-5-carboxamide by reaction with peroxyacetic acid in the presence of a metal catalyst in a substantially inert solvent.

21. A process according to claim 19, wherein the metal catalyst used in the oxidation reaction is selected from manganese dioxide, manganese (III) acetate, potassium permanganate, cobalt (II) chloride, potassium dichromate and sodium dichromate.

22. A process according to claim 19, wherein the metal catalyst used in the oxidation reaction is supported on an inert support, selected from silica gel, alumina, clay and molecular sieves.

23. A process according to claim 19, wherein the substantially inert solvent used in the oxidation reaction is a chlorinated hydrocarbon solvent.

24. A process for the production of 11a,10b-dihydro-6H-dibenz[b,f]oxireno[d]azepine-6-carboxamide by the reaction of carbamazepine with peroxyacetic acid and a metal catalyst in a substantially inert solvent.

25. A process according to claim 24, wherein the metal catalyst is manganese (III) salen or potassium permanganate.

26. A process according to claim 24, wherein the metal catalyst used in the reaction of carbamazepine is supported on an inert support selected from the group consisting of silica gel, alumina, clay and molecular sieves.

27. A process according to claim 24, wherein the reaction of carbamazepine is carried out in the presence of an inorganic base selected from the group consisting of sodium acetate, sodium carbonate and potassium carbonate.

28. A process according to claim 24, wherein the substantially inert solvent used in the reaction of carbamazepine is a chlorinated hydrocarbon solvent.

* * * * *